(12) United States Patent
Prasad (10) Patent No.: US 10,369,179 B2
(45) Date of Patent: Aug. 6, 2019

(54) **COMPOSITION OF *MANGIFERA INDICA***

(71) Applicant: Kodimule Shyam Prasad, Bangalore (IN)

(72) Inventor: Kodimule Shyam Prasad, Bangalore (IN)

(73) Assignee: Vidya Herbs, Inc., Fullerton, CA (US)

( * ) Notice: Subject to any disclaimer, the term of this patent is extended or adjusted under 35 U.S.C. 154(b) by 340 days.

(21) Appl. No.: 14/852,604

(22) Filed: Sep. 13, 2015

(65) Prior Publication Data

US 2017/0071993 A1 Mar. 16, 2017

(51) Int. Cl.
*A61K 36/22* (2006.01)
*A61K 31/7048* (2006.01)
*A61K 31/353* (2006.01)
*A61K 9/00* (2006.01)

(52) U.S. Cl.
CPC ............ *A61K 36/22* (2013.01); *A61K 9/0053* (2013.01); *A61K 31/353* (2013.01); *A61K 31/7048* (2013.01)

(58) Field of Classification Search
None
See application file for complete search history.

(56) References Cited

U.S. PATENT DOCUMENTS

| | | | |
|---|---|---|---|
| 2006/0088560 A1* | 4/2006 | Charrier | A61K 8/602 424/401 |
| 2011/0046077 A1* | 2/2011 | Talamond | C07H 1/08 514/23 |

FOREIGN PATENT DOCUMENTS

| | | |
|---|---|---|
| CA | 2358013A1-1 | 7/2000 |
| CN | 102920696 A | 2/2013 |
| JP | 2011184351 A2 | 9/2011 |
| WO | WO 2014/138426 A2 | 9/2014 |

OTHER PUBLICATIONS

Aguirre et al. (2011) The Open Nutraceuticals Journal, 4, 189-198 (Year: 2011).*
Bhardwaj et al. (2014) Cardiovasc. Toxicol. 14: 41-51. (Year: 2014).*
Hussain et al. (2012) International Journal of Diabetes Research, 1(3): 32-35. (Year: 2012).*
Li et al. (2010) Phytother. Res. 24: 893-899. (Year: 2010).*
Ling et al. (2009) Food Chemistry 113: 1154-1159. (Year: 2009).*
Shah et al. (2010) Pharmacogn. Rev. 4(7): 42-48. (Year: 2010).*
Nagao et al. (2008) Obesity 17, 310-317. (Year: 2008).*
Rizvi et al. (2001) J. Physiology and Pharmacology, 52, 3, 483-488. (Year: 2001).*
Evans Shirley F et al: "Mango supplementation improves blood glucose in obese individuals.", Nutrition and Metabolic Insights 2014, vol. 7, Jul. 3, 2014 (Jul. 83, 2014), pp. 77-84.
Edralin A. Lucas et al: 11 Mango modulates body fat and plasma glucose and lipids in mice fed a high-fat diet 11, British Journal of Nutrition, vol. 106, No. 10, Jun. 28, 2011 (Jun. 28, 2011), pp. 1495-1505.
Ling Lt et al: 11 Standardised Mangifera indica extract is an ideal antioxidant 11, Food Chemistry, Elsevier LTD, NL, vol . 113, No. 4, Apr. 15, 2009 (Apr. 15, 2009), pp. 1154-1159.
C.M. Ajila et al: "Characterization of bioactive compounds from raw and ripe Mangifera indica L. peel extracts", Food and Chemical Toxicology., vo 1 . 48, No. 12, Dec. 1, 2010 (Dec. 1, 2010), pp. 3406-3411.
National Biodiversity Authority, The Biological Diversity Act, 2002.†

* cited by examiner
† cited by third party

*Primary Examiner* — Christopher R Tate
*Assistant Examiner* — Russell G Fiebig
(74) *Attorney, Agent, or Firm* — TMB Law (57) ABSTRACT

The invention relates to a herbal composition derived from *Mangifera indica*. Methods of making and using the composition for the management of obesity are also contemplated.

5 Claims, 5 Drawing Sheets

COMPOSITION OF *MANGIFERA INDICA*

FIELD OF THE INVENTION

The invention generally relates to a herbal composition. More particularly, the invention relates to a herbal composition derived from *Mangifera indica* and methods for making and using the composition in the treatment and management of obesity and other metabolic conditions.

BACKGROUND

*Mangifera indica* is a large evergreen tree belonging to Anacardiaceae which is native to tropical Asia and has been cultivated in the Indian subcontinent for over 4,000 years. Chemical constituents of *Mangifera indica* are of interest especially the polyphenolics, flavonoids and triterpenoids. The bark is reported to contain protocatechic acid, catechin, mangiferin, alanine, glycine, γ-aminobutyric acid, kinic acid, and shikimic acid. Extract of *Mangifera indica* leaves revealed the presence of steroids, flavonoids, reducing sugar and cardiac glycosides in hexane extracts; anthraquinone, tannin and reducing sugar in the ethyl acetate extracts; and saponin, steroids, tannins, flavonoids, reducing sugars and cardiac glycosides in methanolic extracts (Aiyelaagbe et al., 2009). *Mangifera indica* fruit skin has been found to be a good source of phytochemicals, such as polyphenols, carotenoids, vitamin E and vitamin C (Ajila et al., 2007a).

Obesity is a condition manifesting almost directly as a consequence of a modern day lifestyle that encompasses a sedentary work culture, a high fat, calorie-rich diet, and dearth of regular exercise or physical activity. Addiction to habit-forming substances such as tobacco and alcohol and high day-to-day stress levels also contribute to obesity. Obesity has reached epidemic proportions globally, with more than 1 billion adults overweight—at least 300 million of them clinically obese—and is a major contributor to the global burden of chronic disease and disability. Ischemic heart disease and cardiovascular diseases are conditions, often referred to as lifestyle diseases, that have obesity as one of their root causes. Ischemic heart disease is the number one cause of death in the world today, according the World Health Organization (WHO). Cardiovascular diseases (CVDs) killed nearly 17 million people in 2011 which amounts to three in every 10 deaths. CVDs are among the top causes of death, in India as well, as per the WHO. The importance of managing obesity is therefore evident.

Often coexisting in developing countries with undernutrition, obesity is a complex condition, with serious social and psychological dimensions, affecting virtually all ages and socioeconomic groups. Obesity and being overweight pose a major risk for other serious chronic diseases, including type 2 diabetes, hypertension, stroke and certain forms of cancer. The health consequences range from increased risk of premature death, to serious chronic conditions that reduce the overall quality of life.

It is, therefore, safe to state that managing obesity would substantially aid in reducing global mortality, increasing life expectancy and increasing quality of life for countless individuals. Dietary changes, exercise and activity, behavioral changes, prescription weight-loss medications and weight-loss surgery are common treatments for managing obesity. The treatment method to be undertaken often depends on the preferred choice of an individual undergoing treatment as well as the level of obesity.

The preferred treatment modality for weight loss is dieting and physical exercise. However, due to busy schedules and sedentary lifestyles, dieting and physical exercise is difficult to practice in a regular manner. Weight loss surgery, on the other hand, is ruled out by a host of the population due to the high costs involved. Therefore, there is a gradual shift towards an increase in the use of drugs.

Drugs used for weight-loss generally alter one of the fundamental processes of the human body such as weight regulation by altering appetite, metabolism or absorption of calories. Orlistat is the only anti-obesity medication that is approved for long-term use by the FDA. It reduces the intestinal fat absorption by inhibiting the pancreatic enzyme lipase. Rimonabant and Sibutramine are the other drugs that had initially been approved for the treatment of obesity, but were eventually banned due to safety concerns. Because of the potential side effects of anti-obesity drugs, it is recommended that they only be prescribed for obesity where it is hoped that the benefits of the treatment will outweigh their risks.

What is needed in the art therefore is a safe, affordable and effective treatment for the management of obesity. The inventor of the present disclosure, therefore, envisages a cost-effective and safe herbal composition derived from *Mangifera indica* for the management of obesity.

SUMMARY OF THE INVENTION

It is an object of the invention to provide a method for managing obesity in a subject comprising administering a composition to the subject, wherein the composition comprises a composition derived from *Mangifera indica* in an amount effective to manage obesity in the subject.

In some aspects of the invention, the composition is derived from *Mangifera indica* extract.

In some aspects of the invention, the amount effective to manage obesity in the subject ranges between 50-1,000 mg/kg body weight.

In some aspects of the invention, the amount effective to manage obesity in the subject ranges between 50-500 mg/kg body weight.

In some aspects of the invention, managing obesity in the subject comprises decreasing at least one of appetite, body weight gain, metabolism and absorption of calories.

In some aspects of the invention, administering the composition to the subject increases insulin levels in the subject.

In some aspects of the invention, administering the composition to the subject reduces lipase activity in the subject.

In some aspects of the invention, administering the composition to the subject inhibits lipid peroxidation in the subject.

In some aspects of the invention, administering the composition to the subject reduces at least one of serum glucose, total cholesterol, triglyceride, and LDL-c levels in the subject.

In some aspects of the invention, administering the composition to the subject increases HDL-c levels in the subject.

In some aspects of the invention, the composition comprises at least one of an extract of *Mangifera indica* bark, *Mangifera indica* leaf, and *Mangifera indica* fruit skin.

In some aspects of the invention, the composition comprises an extract of *Mangifera indica* bark, *Mangifera indica* leaf, and *Mangifera indica* fruit skin in a ratio of about 8:1:1 by weight respectively.

In some aspects of the invention, the composition comprises, by weight, about 29% flavonoids and about 19% polyphenols.

In some aspects of the invention, the composition comprises flavonoids and polyphenols in a ratio of about 1.5:1 by weight respectively.

In some aspects of the invention, the composition comprises, by weight, about 22% mangiferin, about 4% catechin, about 3% epicatechin, and about 0.4% quercitin dihydrate.

In some aspects of the invention, the composition comprises mangiferin, catechin, epicatechin, and quercitin dehydrate in a ratio of about 55:10:7.5:1 by weight respectively.

In some aspects of the invention, administering the composition to the subject inhibits super oxide dismutase in the subject.

In some aspects of the invention, the composition is administered as a powder, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol or injection.

It is a further object of the invention to provide a composition for managing obesity in a subject, wherein the composition is derived from *Mangifera indica*.

In some aspects of the invention, the composition is derived from *Mangifera indica* extract.

In some aspects of the invention, the composition comprises an extract of at least one of *Mangifera indica* bark, *Mangifera indica* leaf, and *Mangifera indica* fruit skin.

In some aspects of the invention, the composition comprises an extract of *Mangifera indica* bark, *Mangifera indica* leaf, and *Mangifera indica* fruit skin in a ratio of about 8:1:1 by weight respectively.

In some aspects of the invention, the composition comprises, by weight, about 29% flavonoids and about 19% polyphenols.

In some aspects of the invention, the composition comprises flavonoids and polyphenols in a ratio of about 1.5:1 by weight respectively.

In some aspects of the invention, the composition comprises, by weight, about 22% mangiferin, about 4% catechin, about 3% epicatechin, and about 0.4% quercitin dihydrate.

In some aspects of the invention, the composition comprises mangiferin, catechin, epicatechin, and quercitin dehydrate in a ratio of about 55:10:7.5:1 by weight respectively.

In some aspects of the invention, the composition comprises a powder, pill, tablet, pellet, capsule, thin film, solution, spray, syrup, linctus, lozenge, pastille, chewing gum, paste, vapor, suspension, emulsion, ointment, cream, lotion, liniment, gel, drop, topical patch, buccal patch, bead, gummy, gel, sol or injection.

DEFINITIONS

Figure 1A:
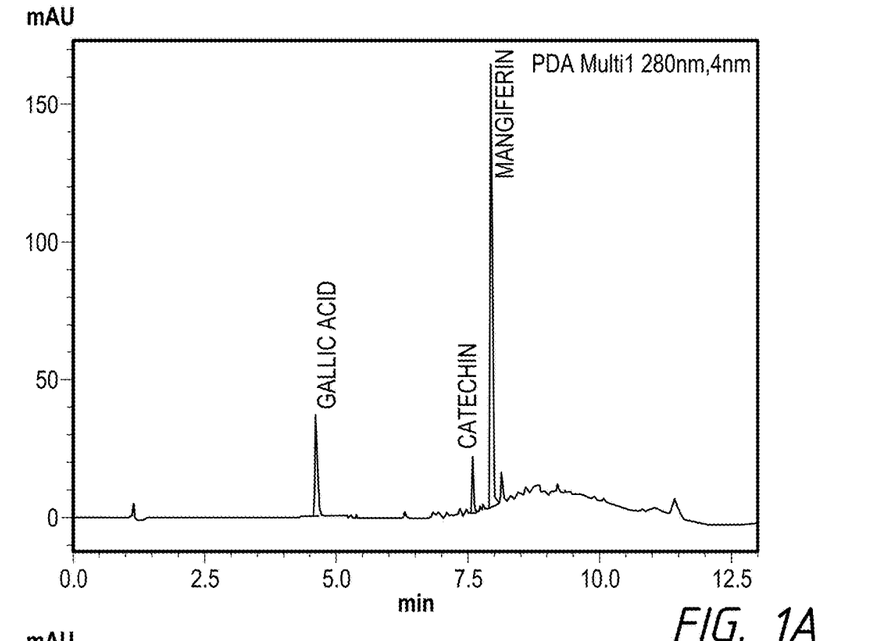
FIG. 1A shows an HPLC chromatogram of a composition of the invention with values for gallic acid, catechin and mangiferin.
Figure 1B:
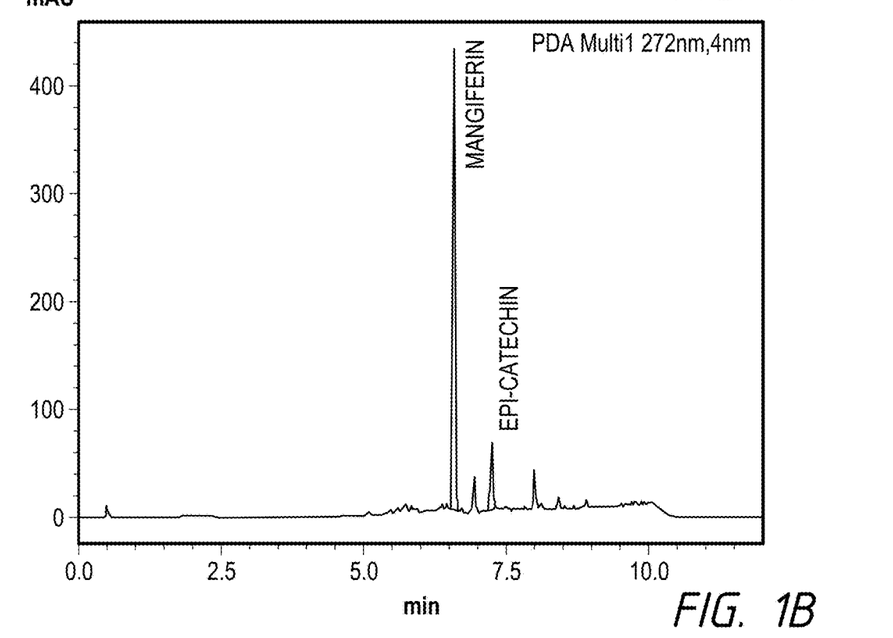
FIG. 1B shows an HPLC chromatogram of a composition of the invention with values for mangiferin and EPI-catechin.
Figure 1C:
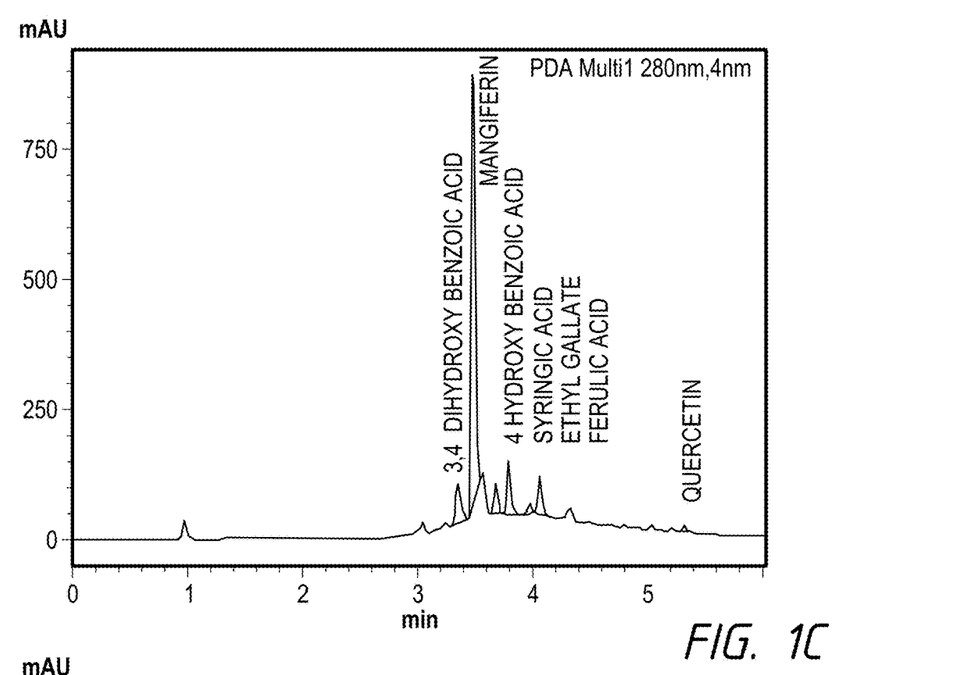
FIG. 1C shows an HPLC chromatogram of a composition of the invention with values for 3,4 dihydroxy benzoic acid, mangiferin, 4 hydroxy benzoic acid, syringic acid, ethyl gallate, ferulic acid, and quercetin.
Figure 1D:
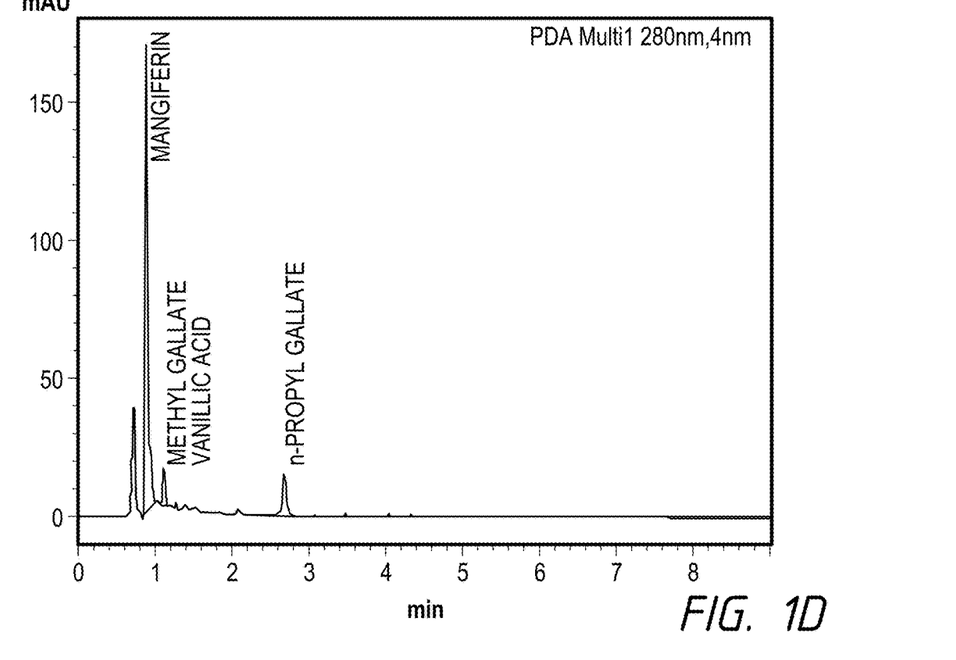
FIG. 1D shows an HPLC chromatogram of a composition of the invention with values for mangiferin, methyl gallate, vanillic acid and n-propyl gallate.
Figure 1E:
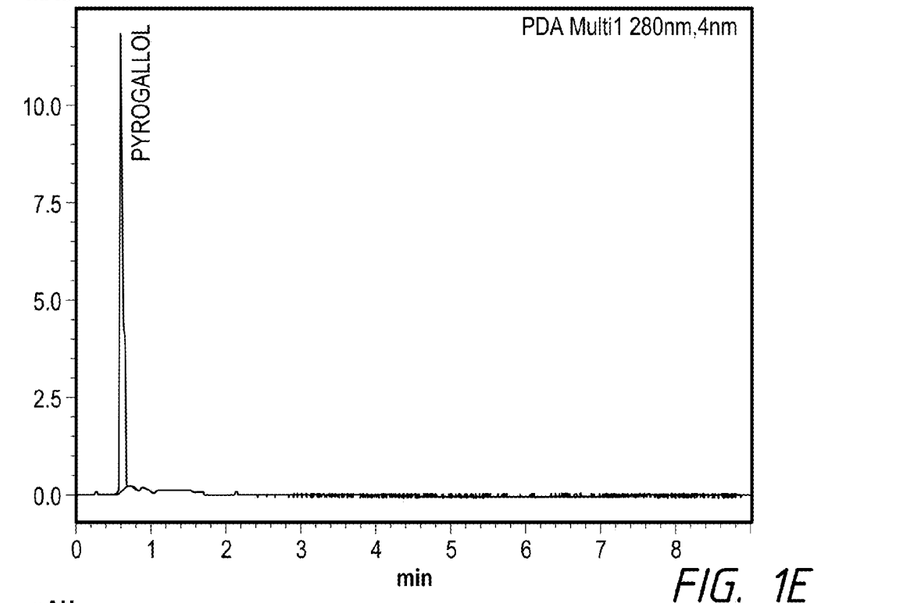
FIG. 1E shows an HPLC chromatogram of a composition of the invention with a value for pyrogallol.
Figure 1F:
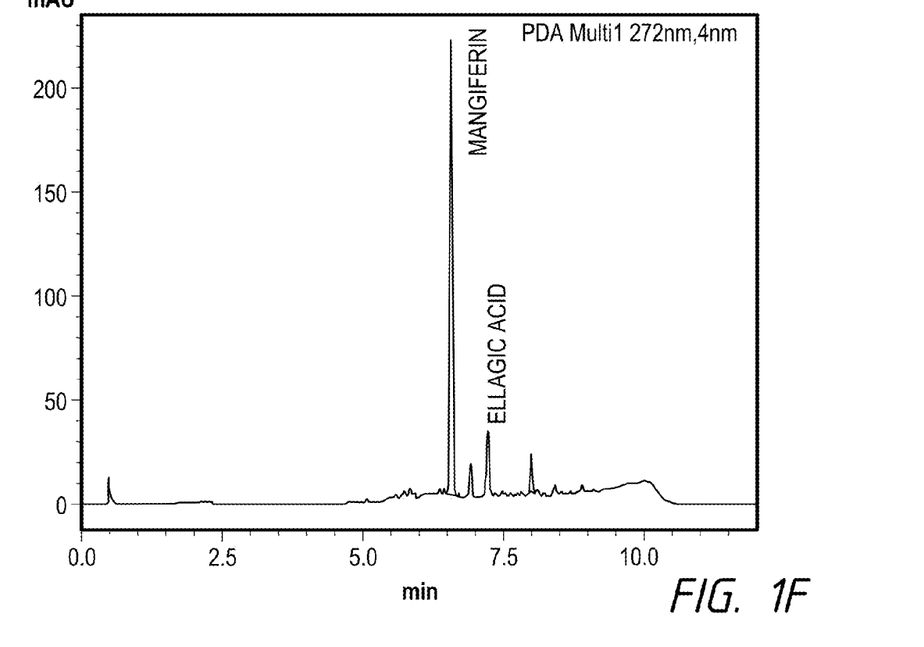
FIG. 1F shows an HPLC chromatogram of a composition of the invention with values for mangiferin and ellagic acid.
Figure 2:
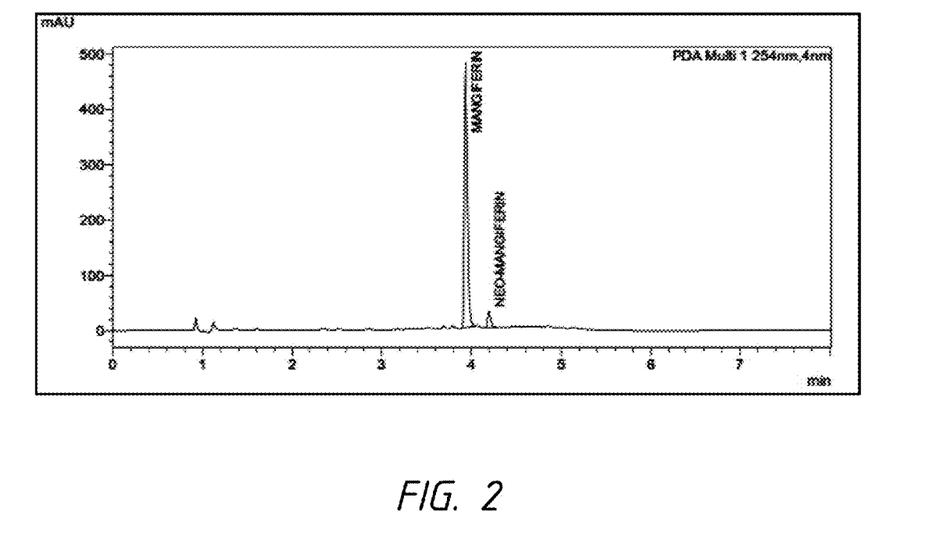
FIG. 2 shows an HPLC chromatogram of a mangiferin composition.
Figure 3:
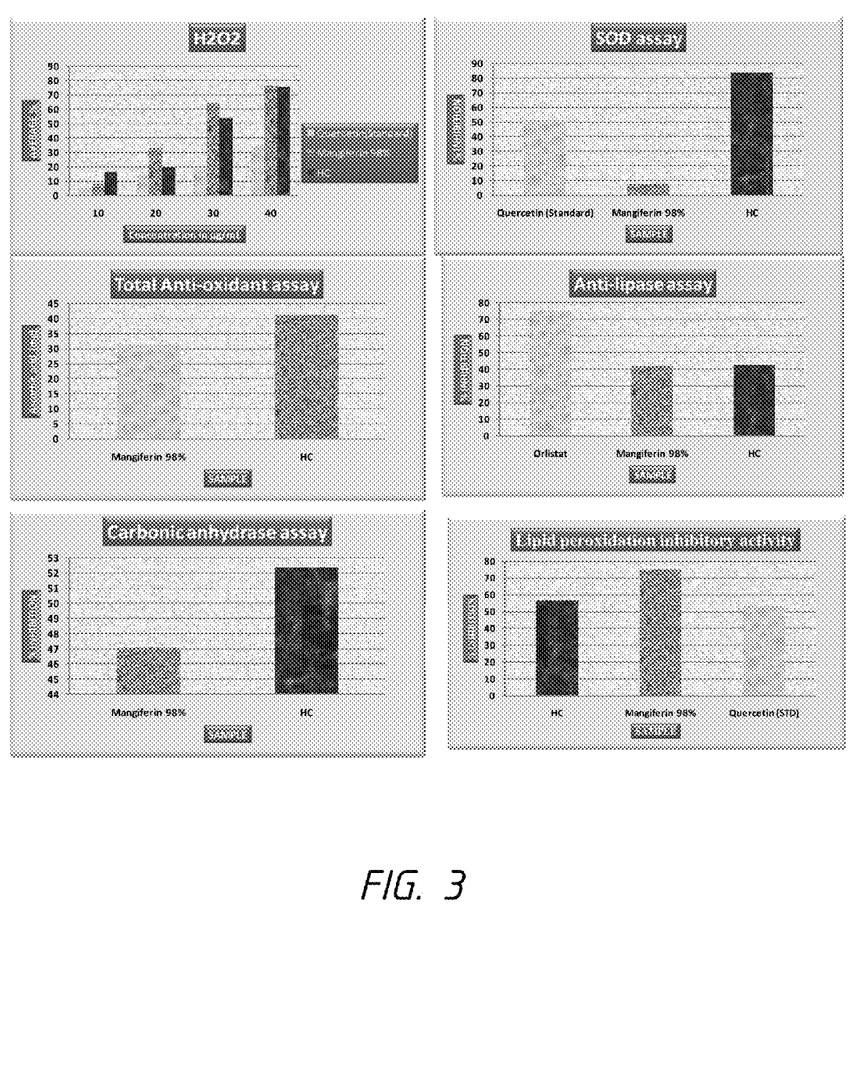
FIG. 3 shows the in-vitro evaluation of $H_2O_2$ scavenging, SOD, anti-oxidant, anti-lipase, lipid peroxidation inhibitory and carbonic anhydrase activity."

The term "about" as used herein refers to a quantity, level, value, number, frequency, percentage, dimension, size, amount, weight or length that varies by as much as 30, 25, 20, 25, 10, 9, 8, 7, 6, 5, 4, 3, 2 or 1% to a reference quantity, level, value, number, frequency, percentage, dimension, size, amount, weight or length. In particular embodiments, the terms "about" or "approximately" when preceding a numerical value indicates the value plus or minus a range of 15%, 10%, 5%, or 1%, or any intervening range thereof.

As used herein, the phrase "*Mangifera indica*" refers to any material from the *Mangifera indica* plant, including, but not limited to, bark, leaves, fruit, seeds, leaves, stems, wood, fruit skin, flowers, pollen, and combinations thereof.

The phrase "body mass index" as used herein refers to a ratio of height to body weight that is calculated as follows:

$$BMI = \frac{mass_{kg}}{(height)^2_m} = \frac{(mass)_{lb}}{(height)^2_{in}} \times 703$$

The terms "obese" and "obesity" as used herein refer to a subject having a body mass index of 30 or higher.

The term "overweight" as used herein refers to a subject having a body mass index of 25 to 29.9.

The term "healthy weight" as used herein refers to a subject having a body mass index of 18.5 to 24.9.

The term "underweight" as used herein refers to a subject having a body mass index of below 18.5.

The term "reduce" as used herein refers to any measurable decrease in a parameter relative to control conditions.

The term "increase" as used herein refers to any measurable increase in a parameter relative to control conditions.

The term "modulate" as used herein refers to an increase or decrease in a referenced parameter.

The phrases "treating obesity," "managing obesity," and the like, refer to preventing or reducing body fat in a subject, preventing or reducing weight gain in a subject, preventing or reducing the absorption of fat from dietary intake in a subject, reducing body mass index (BMI) in a subject, reducing abdominal fat in a subject, preventing weight gain in a subject from a high fat diet and combinations thereof.

As used herein, the term "subject" refers to a mammalian subject, including humans, cattle, horses, sheep, pigs, poultry, dogs, or cats. In a preferred embodiment, the subject is a human subject.

DETAILED SPECIFICATION

The invention generally relates to a herbal composition and methods for its use in a variety of therapeutic and preventative applications. More particularly, the invention relates to a composition derived from *Mangifera indica* and methods for its use and manufacture in the management of obesity.

The composition may be derived from any *Mangifera indica* material capable of providing a composition having the effects described herein. The composition may be derived from bark, wood, seeds, leaves, stems, fruit, fruit skin, stalks, flowers, pollen, roots, or a combination thereof, or an extract of any of the foregoing. The composition of the invention can be prepared from *Mangifera indica* bark, *Mangifera indica* leaves, and *Mangifera indica* fruit skin. The composition of the invention can be prepared from *Mangifera indica* bark, *Mangifera indica* leaves, and *Man-*

*gifera indica* fruit skin in a ratio of about 8:1:1 by weight respectively. The composition of the invention can be prepared from an extract of *Mangifera indica* bark, an extract of *Mangifera indica* leaves, and an extract of *Mangifera indica* fruit skin in a ratio of about 8:1:1 by weight respectively.

The composition may comprise flavonoids and/or polyphenols obtained from *Mangifera indica*. Such flavonoids and/or polyphenols may comprise purified flavonoids and/or purified polyphenols. The composition may comprise at least one of mangiferin, catechin, epicatechin, quercetin dehydrate. The composition may comprise at least one of purified mangiferin, purified catechin, purified epicatechin, and purified quercetin dehydrate. The composition can comprise, by weight, about 22% mangiferin, about 4% catechin, about 3% epicatechin, and about 0.4% quercitin dihydrate. The composition may comprise mangiferin, catechin, epicatechin, and quercitin dehydrate in a ratio of about 55:10:7.5:1 by weight respectively. Polyphenols of the composition can be one or more of gallic acid, 3, 4-Dihydroxy benzoic acid, methyl gallate, propyl gallate, pyrogallol, parahydroxy benzoic acid, vanillic acid, syringic acid, ferulic acid, ethyl gallate, and ellagic acid. The composition can comprise an extract of *Mangifera indica* combined with one or more polyphenols (e.g. purified polyphenols) and flavonoids (e.g. purified flavonoids).

The composition may be formulated to achieve one or more of the effects described herein. Such effects include, but are not limited to, managing obesity, reducing BMI in a subject, reducing body fat in a subject, and/or inhibiting lipase activity in a subject. One skilled in the art will appreciate that methods for measuring the inhibition of lipase are known in the art and include, for example, in vitro lipase enzyme assays.

The herbal composition of the present invention finds use in a variety of therapeutic and preventive applications. In some embodiments of the invention, the herbal composition is administered to a subject for preventing oxidation (antioxidant activity). In other embodiments of the invention, the herbal composition finds use in treating, preventing or managing obesity. In embodiments of the invention, the herbal composition is administered in the management of hyperlipidemic conditions, including but not limited to, reducing serum low density lipids, cholesterol and triglycerides, raising high density lipids (HDL) and combinations thereof. In other embodiments of the invention, the herbal composition is administered to prevent or reduce the accumulation of fat in the liver. In other embodiments, the herbal composition of the invention is administered to reduce oxidative stress or to regulate blood glucose levels. The term "reduce" as used herein refers to any measurable decrease that is produced as a result of administering the composition of the invention, relative to the absence of such administration. Significantly, the composition of the invention is non-toxic and non-mutagenic. Similarly, the term "increase," or "raise," refers to any measurable increase that is produced as a result of administering the composition of the invention, relative to the absence of such administration. In some embodiments, the composition is administered to a subject for preventing oxidation and the production of free radicals in the subject (i.e. antioxidant activity). Thus, the composition may have a nutritive effect for maintaining and promoting health in a subject.

The composition of the invention finds use in treating or managing obesity in a subject. The composition may be administered to an obese subject in an amount effective to reduce body fat in the subject. The composition may be administered to an obese subject in an amount effective to reduce body mass index (BMI) in the subject. The composition may be administered to an overweight subject in an amount effective to reduce body fat in the subject. The composition may be administered to an overweight subject in an amount effective to reduce body mass index (BMI) in the subject. The composition may be administered as an appetite suppressant. Accordingly, the composition may be administered to an obese, overweight, healthy weight or underweight subject to suppress the appetite of the subject. The composition can be administered to produce thermogenesis in a subject, wherein the subject is an obese, overweight, healthy weight or underweight subject.

In some aspects, the composition is administered to reduce the BMI or body fat level in a subject. The composition may be administered to reduce the BMI or body fat level in an obese subject. The composition may be administered to reduce the BMI or body fat level in an overweight subject. The composition may be administered to reduce the BMI or body fat level in a healthy weight subject. The composition may be administered to reduce the BMI or body fat level in an underweight subject.

In some aspects, the composition is administered to maintain the BMI or body fat level in a subject. That is, the composition is administered to keep the BMI or body fat of the subject at their BMI or body fat level at the time the composition is administered. The composition may be administered to maintain the BMI or body fat level in an obese subject. The composition may be administered to maintain BMI or body fat level in an overweight subject. The composition may be administered to maintain BMI or body fat level in a healthy weight subject. The composition may be administered to maintain BMI or body fat level in an underweight subject.

In some aspects of the invention, the composition is administered to prevent an increase in BMI or body fat in a subject. The composition may be administered to prevent an increase in BMI or body fat in an obese subject. The composition may be administered to prevent an increase in BMI or body fat in an overweight subject. The composition may be administered to prevent an increase in BMI or body fat in a healthy weight subject. The composition may be administered to prevent an increase in BMI or body fat in an underweight subject.

In some aspects, the composition is used to treat diabetes in a subject in need thereof. Accordingly, the composition can be used to treat the symptoms of diabetes by increasing insulin levels in a subject in need thereof, and/or reducing serum glucose levels in a subject in need thereof.

Another aspect of the invention concerns the dosage of the herbal composition that is administered to the subject. The dosage of the composition will depend on the nature of the condition to be treated or managed, and the degree or advancement of the condition being addressed. Some non-limiting examples of dosages for use with the invention include about 50-1,000 mg/kg body weight. In one aspect of the invention, the dosage is about 500 mg/kg body weight.

The composition may be administered at a dose of between about 5 mg/day to about 500 mg/day. The composition may be administered at a dose between about 20 mg/day to about 1 mg/day. The composition of the invention may be administered at a dose of about 20 mg/day, about 21 mg/day, about 22 mg/day, about 23 mg/day, about 24 mg/day, about 25 mg/day, about 26 mg/day, about 27 mg/day, about 27 mg/day, about 28 mg/day, about 29 mg/day, about 30 mg/day, about 31 mg/day, about 32 mg/day, about 33 mg/day, about 34 mg/day, about 35 mg/day, about 40 mg/day, about 45 mg/day, about 50 mg/day, about 100 mg/day, about 150 mg/day, about 200 mg/day, about 250 mg/day, about 300 mg/day, about 350 mg/day, about 400 mg/day, about 450 mg/day, or about 500 mg/day, as well as any dosage intervening these specifically disclosed amounts. The composition may be administered at a dosage of between about 400 mg/day to about 500 mg/day, between about 300 mg/day to about 400 mg/day, between about 200 mg/day to about 300 mg/day, between about 100 mg/day to about 200 mg/day, between about 100 mg/day to about 200 mg/day, or about 20 mg/day to about 100 mg/day. The composition may be administered at about 50 mg/kg body weight, 100 mg/kg body weight, 150 mg/kg body weight, 200 mg/kg body weight, 250 mg/kg body weight, 300 mg/kg body weight, 350 mg/kg body weight, 400 mg/kg body weight, 450 mg/kg body weight, 500 mg/kg body weight, 550 mg/kg body weight, 600 mg/kg body weight, 650 mg/kg body weight, 700 mg/kg body weight, 750 mg/kg body weight, 800 mg/kg body weight, 850 mg/kg body weight, 900 mg/kg body weight, 1,000 mg/kg body weight, 1,500 mg/kg body weight, or about 2,000 mg/kg body weight. It is contemplated that the composition may be administered at any dosage that intervenes the dosages called out in this specification. The dosages disclosed in this specification may be administered between one and four times daily. In one aspect of the invention, the selected dosage is administered three times a day.

The herbal composition of the present invention may be administered by various routes including but not limiting to topical, oral, buccal, sub-lingual, parenteral, rectal, and inhalation. The composition may be in a dosage form that includes but is not limited to powders, pills, tablets, pellets, capsules, thin films, solutions, liquids, sprays, syrups, linctuses, lozenges, pastilles, chewing gums, pastes, vaporizers, suspensions, emulsions, ointments, creams, lotions, liniments, gels, drops, topical patches, buccal patches, beads, gummies, gels, sols, injections and the like. Typically, the composition comprises at least one pharmaceutically acceptable excipient.

The composition of the invention can comprise one or more agents for improving the palatability of the composition. For example, the composition may comprise at least one sweetener, aromatic compound, flavoring, or a combination thereof. Similarly, the composition of the invention may comprise agents to increase the antioxidant and/or nutritional value of the compositions. Such agents include, but are not limited to, vitamins, minerals, proteins, amino acids, and carbohydrates.

Another aspect of the invention concerns methods for making the subject composition. In some aspects, the composition are made by ethanol extraction of *Mangifera indica*. In other aspects of the invention, the composition is made by aqueous extraction *Mangifera indica*. In still other embodiments, the composition of the invention is prepared by compressing a *Mangifera indica* material to obtain the liquid component of *Mangifera indica*.

The present disclosure is further described in the light of the following non-limiting examples which are set forth for illustration purpose only and not to be construed for limiting the scope of the disclosure.

EXAMPLE 1

Procedure for Preparation of the Composition

Dried parts of *Mangifera indica* bark, leaf and fruit skin (8:1:1 ratio) were cut in to small pieces, approximately 10 mm in length, to form a 100 kg mass. This mass was pulverized to form a coarse powder in a hammer mill and stacked in a vertical 1.0 KL extractor. The lower end of the extractor contained a perforated plate on which a filtration cloth was fixed. The bottom of the extractor was connected to a transfer pump input and the output of the transfer pump was connected to a T bend. One end was connected to the extractor top for circulation of the extraction mass during the extraction period and the other end of the T bend was connected to a receiver tank.

The above-mentioned coarse powder was initially extracted with six bed volumes of 70% v/v ethyl alcohol. The extraction was carried out at 75-78° C. for about 7-8 hours with continuous circulation of the extract with a transfer pump. After completion of extraction, the extract was filtered through a 5 micron SS candle filter and the resultant clear extract was collected in a receiver tank. The bed was re-extracted by adding 4 bed volumes of 70% ethyl alcohol 3 more times at a temperature of 75-78° C. for about 7-8 hours. All the extracts were then collected in a receiver tank and the combined extract was concentrated in a reactor under vacuum at 80-85° C. till the extract mass-total dissolved solids (TDS) reached 60-70%. The extract mass was further dried in a vacuum tray drier at 80-85° C. until the completion of drying. The yield of the extract, the herbal composition was found to be 14±0.5 w/w %. The extract was further subjected to phyto-chemical analysis through spectrophotometric and HPLC estimations. The studies confirmed that the composition is associated with good percentage of antioxidant constituents.

TABLE 1

Results of phyto-chemical analysis

| S.N. | Phyto-constituents | Percentage | Analysis Method |
|---|---|---|---|
| 1 | Total flavonoids | 28.56 ± 0.93 w/w % | Spectrophotometric |
| 2 | Total polyphenols | 18.9 ± 1.8 w/w % | Spectrophotometric |

The composition of the total flavonoids was determined by the HPLC method and the following results were obtained:

TABLE 2

Composition of the determined flavonoids

| S.N. | Constituents | Percentage |
|---|---|---|
| 1 | Mangiferin | 21.5 ± 0.82 w/w % |
| 2 | (+)-Catechin | 3.84 ± 0.31 w/w % |
| 3 | (−)-Epicatechin | 2.67 ± 0.25 w/w % |
| 4 | Quercetin dihydrate | 0.43 ± 0.06 w/w % |

The composition of the total polyphenols was determined by the HPLC method and the following results were obtained:

TABLE 3

Composition of the determined polyphenols

| S.N. | Constituents | Percentage |
|---|---|---|
| 1 | Gallic acid | 4.5 ± 0.42 w/w % |
| 2 | 3,4-Dihydroxy benzoic acid | 0.93 ± 0.23 w/w % |
| 3 | Methyl gallate | 1.2 ± 0.34 w/w % |
| 4 | Proplyl gallate | 2.31 ± 0.73 w/w % |
| 5 | Pyrogallol | 0.48 ± 0.08 w/w % |
| 6 | Parahydroxy benzoic acid | 1.43 ± 0.07 w/w % |
| 7 | Vanillic acid | 0.33 ± 0.06 w/w % |
| 8 | Syringic acid | 0.82 + 0.13 w/w % |
| 9 | Ferulic acid | 0.12 ± 0.02 w/w % |
| 10 | Ethyl gallate | 0.76 ± 0.14 w/w % |
| 11 | Ellagic acid | 0.16 ± 0.05 w/w % |

TABLE 4

Peak Table showing phenolic and flavonoids in composition

| Name | Ret. Time | Area | Height | Area % | Lambda max |
|---|---|---|---|---|---|
| Mangiferin | 3.936 | 1120914 | 479844 | 94.067 | 257/241/318/366/580 |
| (+)-Catechin | 7.598 | 58049 | 20738 | 9.623 | 203/278/366/657/622 |
| (−)-Epicatechin | 7.245 | 197931 | 62255 | 15.075 | 208/274/662/623 |
| Quercetin dihydrate | 5.314 | 29209 | 12881 | 1.038 | 254/370/199 |
| Gallic acid | 4.629 | 132932 | 36837 | 22.038 | 215/270/387/656/404 |
| 3,4-Dihydroxybenzoic acid | 3.352 | 245290 | 75658 | 8.716 | 260/206/222/295/365 |
| Methyl gallate | 1.114 | 32395 | 13176 | 6.362 | 215/271 |
| Proplyl gallate | 2.680 | 53767 | 15055 | 10.559 | 216/273 |
| Pyrogallol | 0.598 | 37015 | 11721 | 100.000 | 202/257/240/315/362 |
| Parahydroxy benzoic acid | 3.683 | 127757 | 54283 | 4.540 | 256/315/198 |
| Vanillic acid | 1.269 | 4780 | 2177 | 0.939 | 204/260 |
| Syringic acid | 3.795 | 211448 | 79433 | 7.513 | 271/226 |
| Ferulic acid | 4.062 | 190504 | 74471 | 6.769 | 261/360 |
| Ethyl gallate | 3.975 | 46246 | 17396 | 1.643 | 261/245 |
| Ellagic acid | 7.990 | 43005 | 18447 | 6.750 | 253/366/662/623 |

EXAMPLE 2

UPLC Analysis for Composition

Reagents Required:

Mangiferin (98% purity) was procured from Sigma Aldrich. Chemicals required for the analysis Acetonitrile (ACN), Methanol (MeOH), Formic acid, double distilled water was of LC grade.

Solution Preparation

Around 10 mg of composition was weighed into a 10 mL standard flask.

Approximately 3 mL of 70% methanol (LC grade) was added. The mixture was sonicated for 10 minutes, and made up to the mark with the same solvent. The sample solution was filtered through a 0.20 µm a nylon filter.

Standard Preparation

Around 10 mg of standard (98%) was weighed into a 10 mL standard flask and dissolved in 70% methanol (LC grade). The mixture was sonicated for 10 minutes, and made up to mark with the same solvent. The sample solution was filtered through a 0.20 µm nylon filter.

UPLC Analysis of Herbal Composition

A sensitive and selective ultra performance liquid chromatography (UPLC) method was used for the fingerprint analysis of the herbal composition. The LC system consisted of a Shimadzu LC MS/MS #8040 system. The column used was SHIM-PACK XR-ODSIII, 5 µm, 150×2.1 mm with mobile phase consisting 0.1% Formic acid in LCMS grade water: Acetonitrile with isocratic gradient system at run time of 8 min. The flow rate was maintained at 0.35 mL/min at 25±2° C. The eluate was monitored at 254 nm. Retention time was as mentioned in Table 5.

TABLE 5

Optimized Chromatographic Conditions

| S. NO | PARAMETERS | SPECIFICATION |
|---|---|---|
| 1 | Instrument | LC MS/MS #8040 |
| 2 | Detector | SPD-M20A PDA |
| 3 | Mobile phase A:B | 0.1% Formic acid in LCMS grade water:Acetonitrile |
| 4 | Column | SHIM-PACK XR-ODSIII, 5 µm, 150 × 2.1 mm |
| 5 | Pump | Nexera X2, LC-30AD Shimadzu |
| 6 | Wavelength | 254 nm |
| 7 | Flow rate | 0.35 mL/min |
| 8 | Volume of injection | 1 µL |
| 9 | Run time | 8 min |

TABLE 6

Peak Table showing mangiferin in the composition

| Name | Ret. Time | Area | Height | Area % | Lambda max |
|---|---|---|---|---|---|
| Mangiferin | 3.936 | 1120914 | 479844 | 94.067 | 257/241/318/366/580 |
| Neo-mangiferin | 4.195 | 70695 | 29923 | 5.933 | 259/243/319/364/579 |
| Total | | 1191609 | 509767 | 100.000 | |

EXAMPLE 3

In-Vitro Evaluation of Composition

Antioxidant Activity Studies:

Hydrogen Peroxide ($H_2O_2$) Scavenging Activity:

Procedure:

Hydrogen peroxide scavenging activity of the composition was estimated in this study where initially, composition solutions were prepared at different concentrations in distilled water and the resultant solutions were mixed in 0.6 ml of 40 mM $H_2O_2$ solution prepared in phosphate buffer (0.1 M pH 7.4) and incubated for 10 min. The absorbance was measured at 230 nm against a blank solution containing $H_2O_2$. Similar procedure was repeated for composition, mangiferin and quercetin. The amount of hydrogen peroxide radical inhibited was calculated using the following equation. The result is expressed as % $H_2O_2$ radical scavenging activity.

$$H_2O_2 \text{ radical scavenging activity} = \left\{ \frac{(\text{Abs control} - \text{Abs control}) \times 100}{(\text{Abs control})} \right\}$$

where:

Abs control—Absorbance of $H_2O_2$ radical

Abs sample—Absorbance of sample extract/standard (the composition, mangiferin and quercetin)

Result:

TABLE 7

| | $H_2O_2$ scavenging activity | | | |
|---|---|---|---|---|
| | Concentration in µg/ml | | | |
| Samples | 10 | 20 | 30 | 40 |
| Quercetin(Standard) | 5.6 | 14.55 | 18.86 | 33.96 |
| Mangiferin 98% | 8.49 | 33.01 | 64.15 | 76.41 |
| Composition | 16.43 | 19.17 | 53.42 | 75.34 |

Conclusion: The composition exhibited good $H_2O_2$ scavenging activity in concentration dependent manner.

Superoxide Dismutase (SOD) Activity:

Procedure:

The superoxide anion scavenging activity of the composition was measured in this test. 1 ml (156 µM) of Nitro blue tetrazolium (NBT), 1 ml (468 µM) of nicotinamide adenine dinucleotide (NADH) and 3 ml of the composition at 100 µg/ml concentration were admixed in phosphate buffer (pH 7.4). The reaction was started by adding 100 µl of phenazine methosulfate (PMS) (0.18 mg/ml) and the mixture was incubated at 25° C. for 5 min followed by measuring the absorbance at 560 nm. Similar solutions were prepared for quercetin and mangiferin and the percentage of inhibition was calculated by using the formula provided herein-below; the result was expressed as % superoxide dismutase scavenging activity.

$$\% \text{ superoxide dismutase inhibition} = \left\{ \frac{(\text{Abs control} - \text{Abs sample}) \times 100}{\text{Abs control}} \right\}$$

where:

Abs control—Absorbance of control

Abs sample—Absorbance of sample extract/standard (the composition, mangiferin and quercetin)

Result:

TABLE 8

| SOD activity results | |
|---|---|
| SOD activity | |
| Sample Concentration in µg/ml | % Inhibition |
| Quercetin (Standard) | 51.03 |
| Mangiferin 98% | 7.50 |
| Composition | 83.40 |

Conclusion: the composition exhibited significant SOD activity in comparison with 98% mangiferin and quercetin.

Total Antioxidant Assay:

Procedure:

The total antioxidant activity of the composition was determined by the phosphomolybdenum method where 0.3 ml of the composition (100 µg/ml) was combined with 3 ml of a reagent solution (0.6M sulfuric acid, 28 mM sodium phosphate and 4 mM ammonium molybdate). The resultant reaction mixture was incubated at 95° C. for 90 min and cooled to room temperature. The absorbance of the solution was measured at 695 nm against a blank solution (water). The total antioxidant capacity was expressed as the milligram equivalents of ascorbic acid.

Result:

TABLE 9

| Total antioxidant assay | |
|---|---|
| Total antioxidant assay | |
| Sample Concentration µg/ml | mg equivalent ascorbic acid |
| Mangiferin 98% | 31.23 |
| Composition | 41.06 |

Conclusion: The total antioxidant capability of the composition was found to be 41.06 mg equivalent ascorbic acid. The composition exhibited good antioxidant property. The antioxidant ability of composition was confirmed through hydrogen peroxide radical scavenging activity, superoxide radical scavenging activity and the total antioxidant capacity.

In Vitro Anti-obesity Studies:

Anti-lipase Assay:

Procedure:

A suspension containing 1% (V/V) of triolein and 1% (V/V) of tween 40 in 0.1M phosphate buffer (pH-8) was prepared and emulsified. The assay was initiated by adding 800 µl of the Triolein emulsion to 200 µl of Porcine Pancreatic Lipase (0.5 g Pancreatic Lipase in 15 ml of 0.1 M phosphate buffer at pH-8) and 200 µl of the composition extract (100 µg/ml concentration). The resultant mixture was mixed and the absorbance was measured immediately at 450 nm ($T^0$). The mixtures were then incubated at 37° C. for 30 min and the absorption was measured at 450 nm ($T^{30}$).

$$\text{Inhibition } \% = \left\{ \frac{A(cont) - A(\text{test}) \times 100}{A(cont)} \right\}$$

where:

A(cont)—is the absorbance of the control ($T_c^0 - T_c^{30}$)

A(test)—is the absorbance of the sample test/standard ($T^0 - T^{30}$) (the composition, mangiferin and quercetin)

Result:

TABLE 10

Anti-lipase assay results
Anti-lipase assay

| Sample Concentration: 1.2 mg/ml | % Inhibition |
|---|---|
| Orlistat | 75.27 |
| Mangiferin 98% | 41.78 |
| Composition | 42.30 |

Conclusion: The composition showed good anti-lipase property.

Carbonic Anhydrase Assay:

Procedure:

The composition at 250 µg/ml and 98% Mangiferin were independently mixed in 1.4 ml of tris buffer and 2.5 ml of carbonic anhydrase. The resultant mixtures were incubated at room temperature for 5 min. After incubation, 1 ml of 4-NPA was added to the mixtures and further incubated for 15-20 min at 37° C. The absorbance of the reaction mixtures were measured at 400 nm.

$$\text{Inhibition \%} = \left\{ \frac{A(cont) - A(\text{test}) \times 100}{A(cont)} \right\}$$

where:
A (cont)—is the absorbance of the control
A (test)—is the absorbance of the test sample/standard Result:

TABLE 11

Carbonic Anhydrase test results
Carbonic Anhydrase

| Sample Concentration: 100 µg | % inhibition |
|---|---|
| Mangiferin 98% | 47.06 |
| Composition | 52.31 |

Conclusion: The composition showed enhanced anti-lipase property as compared to Mangiferin.

Lipid Peroxidation Inhibitory Assay:

Procedure:

A modified thiobarbituric acid reactive species (TBARS) assay (Ohkowa et al., 1979) is used to measure lipid peroxidation formed using egg yolk homogenate as lipid rich media (Ruberto et al., 2000).

Take 0.5 ml of egg homogenate (10% in distilled water) and 0.1 ml of test sample in the concentration range 100-500 µg/ml in a test tube and volume made up to 1 ml by adding distilled water. Finally add 0.05 ml ferrous sulphate (0.07M) to the above mixture and incubate for 30 min to induce the lipid peroxidation. Thereafter add 1.5 ml of 20% acetic acid (pH 3.5) and 1.5 ml of (0.8% in 1.1% SDS) TBA and 0.05 ml (20%) TCA then heated in boiling water bath for 60 min. After cooling 5 ml of butanol will be added to all the test tubes and centrifuged at 3000 rpm for 10 min. Measure the absorbance of the organic upper layer at 532 nm. The percentage inhibition of lipid peroxidation calculated from the formula, $$\text{\% Inhibition} = \frac{(Ab_{control} - Ab_{test\ sample}) * 100}{Ab_{control}}$$

where:
Ab (cont)—is the absorbance of the control
Ab (test sample)—is the absorbance of the test sample/standard

TABLE 12

Lipid peroxidation inhibitory assay test results
Lipid peroxidation inhibitory assay

| Sample Concentration: 100-500 µg/ml | % inhibition |
|---|---|
| Composition | 56.52 |
| Mangiferin 98% | 74.9 |
| Quercetin (STD) | 53.44 |

Conclusion: The composition showed enhanced lipid peroxidation property as compared to Quercetin. Herbal composition possesses good hypolipidemic and anti-obesity activity, which may be due to its antioxidant and free radical scavenging potential.

EXAMPLE 4

Acute Oral Toxicity Study in Rats with the Composition

Single-dose oral toxicity of the composition was evaluated in albino Wistar rats. A limit test was performed in which female rats received a single oral administration of the composition at a dose of 2000 mg/kg body weight. Following dosing, the limit test rats were observed daily and weighed weekly. A gross necropsy examination was performed on all limit test animals at the time of scheduled euthanasia (day 14). No mortality occurred during the duration of the limit test. Further, no significant gross internal findings were observed at necropsy on study day 14.

Conclusion: Under the conditions of this test, the acute oral lethal dose ($LD_{50}$) of the composition was estimated to be greater than 2000 mg/kg in rats.

Repeated Dose 28 Day Oral Toxicity Study of the Composition

Repeated dose 28 day oral toxicity study, with the composition in rats followed by 14 day recovery period, was performed. The objective of the study was to assess the safety of the composition when administered orally to female and male rats. Another objective was to determine the target organ toxicity, no observed effect level (NOEL) and reversibility of signs of toxicity after the recovery period.

Wistar female and male rats were treated with the composition 250, 500 and 1000 mg/kg/b.w for 28 days by oral gavage, followed by 14 day recovery period.

Results: 1) all the male and female animals from control and all the treated dose groups up to 1000 mg/kg survived throughout the dosing period of 28 days and the recovery period of 14 days; 2) no signs of intoxication were observed in male and female animals from different dose groups during the dosing period of 28 days and during the recovery period of 14 days; 3) male rats showed a significant decrease in body weight gain with 250 and 500 mg/kg b.w. of the composition and a significant decrease in body weight gain were seen with 500 and 1000 mg/kg b.w. of the composition in females when compared with the control on day 29. During the reversal period the animals restored to normal when compared with control reversal group on day 43; 4) food consumption of control and treated animals was found to be comparable throughout the dosing period of 28 days and the recovery period of 14 days; 5) hematological analysis conducted at the end of the dosing period on day 29 and at the end of recovery period on day 43, revealed no abnormalities attributable to the treatment; 6) biochemical analysis conducted at the end of the dosing period on day 29 and at the end of recovery period on day 43, revealed no attributable changes to the treatment, except there was a significant increase in high density lipoproteins (HDL) levels in female rats treated with 250, 500 and 1,000 mg/kg/b.w. of the composition; 7) functional battery observation tests conducted at termination revealed no abnormalities; 8) urine analysis, conducted at the end of the dosing period in week 4 and at the end of recovery period in week 6, revealed no abnormality attributable to the treatment; 9) organ weight data of male and female sacrificed at the end of the dosing period and at the end of the recovery period was found to be comparable with that of respective controls, gross pathological examination did not reveal any abnormality; histopathological examination did not reveal any major abnormality except congestion of blood vessels in few organs.

Conclusion: Based on the above findings, the no observed adverse effect level (NOAEL) of the composition was found to be 1000 mg/kg/b.w. for both female and male Wistar rats when given orally for 28 days followed by a 14 day recovery period.

EXAMPLE 5

Anti-Obesity Activity of the Composition W.R.T Standard

Objective: The objective was to investigate the effect of the composition against high fat diet fed rats.

Procedure:

Animals: Male Wistar rats (160 to 200 g); No of animals: 36; Housing: 3/cage, 12 hrs light/dark cycle; Temperature: 25±2° C.;

Model & Composition of the Diet: High fat diet in rats: 25% Lard, 5% Soybean oil; 5% starch; 65% Normal commercial available rat feed;

Groups: Male Wistar rats were divided into six groups with six animals in each group

| Group | Diet |
| --- | --- |
| Group 01: | Normal feed + Vehicle (distilled water) |
| Group 02: | High fat diet |
| Group 03: | High fat diet + Standard drug (Orlistat 30 mg/kg) |
| Group 04: | High fat diet + composition (50 mg/kg) |
| Group 05: | High fat diet + composition (100 mg/kg) |
| Group 06: | High fat diet + composition (150 mg/kg) |

Results:
Effect of the Composition on Body Weight Gain in Male Rats:

TABLE 13

Results of the effect of the composition on body weight gain in male rats

| Groups | Final weight | Initial weight | Difference in body weight gain |
| --- | --- | --- | --- |
| Group I | 251.70 ± 2.02 | 181.70 ± 1.99 | 70.00 ± 2.60 |
| Group II | 292.50 ± 1.81 | 181.50 ± 1.31 | 111.0 ± 2.20***[a] |
| Group III | 261.80 ± 2.53 | 182.00 ± 0.96 | 79.82 ± 2.58***[b] |
| Group IV | 254.80 ± 1.87 | 182.30 ± 1.99 | 72.43 ± 3.16***[b] |
| Group V | 250.50 ± 2.53 | 183.30 ± 0.88 | 67.15 ± 2.75***[b] |
| Group VI | 259.20 ± 6.06 | 184.70 ± 0.80 | 74.50 ± 5.77***[b] |

Values are expressed in terms of SEM ± Mean. Data were analyzed by one way ANOVA followed by Dunnett's t test.
Number of animals in each group n = 6.
[a]Comparison made with control group.
[b]Comparison made with high fat diet group
***$P < 0.001$.

Conclusion: The composition at all doses showed significant reduction ($P<0.001$) in body weight gain when compared to the high fat diet group.

Effect of the Composition on the Average Food Intake in Male Rats:

TABLE 14

Results of the effect of the composition on the average food intake in male rats

| Groups | Average food intake g/rat |
| --- | --- |
| Group I | 17.21 ± 0.38 |
| Group II | 13.56 ± 0.36***[a] |
| Group III | 13.45 ± 0.28[nsb] |
| Group IV | 12.13 ± 0.24**[b] |
| Group V | 11.26 ± 0.24***[b] |
| Group VI | 13.18 ± 0.31[nsb] |

Values are expressed in terms of SEM ± Mean. Data were analyzed by one way ANOVA followed by Dunnett's t test.
Number of animals in each group n = 6.
[a]Comparison made with control group.
[b]Comparison made with high fat diet group.
***$P < 0.001$
***$P < 0.001$
**$P < 0.01$
[ns]non significant.

Conclusion: The composition at 50 and 100 mg/kg b.w showed significant reduction ($P<0.01$, $P<0.001$) in food intake when compared to the high fat diet group.

Effect of the Composition on Liver Organ Weight and Mesenteric, Brown Adipose Tissue (BAT), Perirenal Fat Pads and Epididymal Fat Pad:

TABLE 15

Results of the effect of the composition on liver organ weight and mesenteric, brown adipose tissue (BAT), perirenal fat pads and epididymal fat pad

| Groups | Liver | Mesenteric fat | BAT | Perirenal fat pad tissue | | Epididymal fat pad | |
| --- | --- | --- | --- | --- | --- | --- | --- |
| | | | | Right | Left | Right | Left |
| Group I | 2.8 ± 0.01 | 0.59 ± 0.02 | 0.13 ± 0.01 | 0.25 ± 0.02 | 0.21 ± 0.01 | 0.38 ± 0.01 | 0.33 ± 0.02 |
| Group II | 3.5 ± 0.15***[a] | 1.14 ± 0.07***[a] | 0.30 ± 0.01***[a] | 1.05 ± 0.13***[a] | 1.07 ± 0.11***[a] | 0.63 ± 0.04***[a] | 0.56 ± 0.05***[a] |
| Group III | 2.8 ± 0.08***[b] | 1.02 ± 0.07[nsb] | 0.28 ± 0.01[nsb] | 0.77 ± 0.08*[b] | 0.77 ± 0.08*[b] | 0.55 ± 0.02[nsb] | 0.52 ± 0.03[nsb] |

TABLE 15-continued

Results of the effect of the composition on liver organ weight and mesenteric, brown adipose tissue (BAT), perirenal fat pads and epididymal fat pad

| Groups | Liver | Mesenteric fat | BAT | Perirenal fat pad tissue | | Epididymal fat pad | |
|---|---|---|---|---|---|---|---|
| | | | | Right | Left | Right | Left |
| Group IV | 2.7 ± 0.07***[b] | 0.80 ± 0.03**[b] | 0.17 ± 0.01***[b] | 0.49 ± 0.01***[b] | 0.44 ± 0.03***[b] | 0.51 ± 0.01*[b] | 0.42 ± 0.01*[b] |
| Group V | 2.8 ± 0.03***[b] | 0.83 ± 0.03**[b] | 0.17 ± 0.01***[b] | 0.47 ± 0.02***[b] | 0.67 ± 0.02***[b] | 0.51 ± 0.02*[b] | 0.39 ± 0.02**[b] |
| Group VI | 2.9 ± 0.02***[b] | 0.84 ± 0.03**[b] | 0.17 ± 0.01***[b] | 0.63 ± 0.07**[b] | 0.69 ± 0.04**[b] | 0.51 ± 0.02*[b] | 0.42 ± 0.03*[b] |

Data were analyzed by one way ANOVA followed by Dunnett's t test.
Number of animals in each group n = 6.
[a]Comparison made with control group.
[b]Comparison made with high fat diet group.
***P < 0.001
**P < 0.01
*P < 0.05
[ns]non significant.

Conclusion: The composition at all doses showed significant reduction (P<0.001) in liver organ weight, Perirenal fat pads and BAT, Mesentric fat (P<0.001), epididymal fat pad (P<0.05) when compared to the high fat diet group.

Effect of the Composition on Serum Glucose, Total Cholesterol, Triglyceride, HDL-c and LDL-c Levels (mg/dL):

TABLE 16

Results of the effect of the composition on serum glucose, total cholesterol, triglyceride, HDL-c and LDL-c levels (mg/dL)

| Groups | Glucose | Total cholesterol | Triglyceride | HDL-c | LDL-c |
|---|---|---|---|---|---|
| Group I | 81.63 ± 2.96 | 47.53 ± 1.15 | 52.61 ± 2.14 | 22.61 ± 0.56 | 14.40 ± 1.51 |
| Group II | 114.20 ± 7.63***[a] | 61.39 ± 2.47***[a] | 104.6 ± 4.16***[a] | 17.27 ± 0.51***[a] | 23.20 ± 2.96*[a] |
| Group III | 92.00 ± 2.89**[b] | 50.91 ± 0.62***[b] | 79.96 ± 1.13***[b] | 21.72 ± 1.22**[b] | 13.20 ± 1.71**[b] |
| Group IV | 96.23 ± 2.72*[b] | 48.96 ± 1.90***[b] | 71.48 ± 5.42***[b] | 23.77 ± 0.99***[b] | 10.89 ± 1.02***[b] |
| Group V | 82.37 ± 2.82***[b] | 48.93 ± 2.23***[b] | 55.92 ± 2.03***[b] | 24.97 ± 0.87***[b] | 12.77 ± 1.75***[b] |
| Group VI | 96.70 ± 0.96*[b] | 52.55 ± 1.42**[b] | 79.77 ± 5.30***[b] | 24.25 ± 0.48***[b] | 12.35 ± 2.13**[b] |

Data were analyzed by one way ANOVA followed by Dunnett's t test.
Number of animals in each group n = 6.
[a]Comparison made with control group.
[b]Comparison made with high fat diet group.
***P < 0.001
**P < 0.01
*P < 0.05

Conclusion: The composition at 50 and 150 mg/kg b.w. showed a significant reduction (P<0.05), at 100 mg/kg b.w. showed significant reduction (P<0.01) in glucose levels when compared to high fat diet group. The composition at 50 and 100 mg/kg b.w. showed a significant reduction (P<0.001), at 150 mg/kg b.w. showed significant reduction (P<0.01) in total cholesterol and low density lipoproteins (LDL) levels when compared to high fat diet group. The composition at all doses showed a significant reduction (P<0.001) in total triglycerides and an increase in the HDL levels when compared to the high fat diet group (Group II).

Effect of the Composition on Atherogenic Index:

TABLE 17

Results of the effect of the composition on atherogenic index

| Group | Atherogenic Index |
|---|---|
| Group I | 1.11 ± 0.08 |
| Group II | 2.57 ± 0.18***[a] |
| Group III | 1.39 ± 0.15***[b] |

TABLE 17-continued

Results of the effect of the composition on atherogenic index

| Group | Atherogenic Index |
|---|---|
| Group IV | 1.07 ± 0.06***[b] |
| Group V | 0.96 ± 0.06***[b] |
| Group VI | 1.17 ± 0.08***[b] |

Data were analyzed by one way ANOVA followed by Dunnett's t test.
Number of animals in each group n = 6.
[a]Comparison made with control group.
[b]Comparison made with high fat diet group
***P < 0.001

Conclusion: The composition at all doses showed a significant reduction (P<0.0001) in atherogenic index when compared to the high fat diet group.

Effect of the Composition on Liver Triglyceride Levels

TABLE 18

Results of the effect of the composition on liver triglyceride levels

| Group | Liver triglycerides |
|---|---|
| Group I | 63.85 ± 0.42 |
| Group II | 96.47 ± 1.67***[a] |
| Group III | 87.77 ± 2.28*[b] |
| Group IV | 78.57 ± 1.93***[b] |
| Group V | 86.47 ± 2.11**[b] |
| Group VI | 85.46 ± 2.31**[b] |

Data were analyzed by one way ANOVA followed by Dunnett's t test.
Number of animals in each group n = 6.
[a]Comparison made with control group.
[b]Comparison made with high fat diet group.
***$P < 0.001$
**$P < 0.01$
*$P < 0.05$ Conclusion: The composition at 50 mg/kg b.w. showed a significant reduction (P<0.001), at 100 & 150 mg/kg b.w. showed significant reduction (P<0.01) in liver triglycerides levels when compared to the high fat diet group.

Effect of the Composition on Insulin Hormonal Levels

TABLE 19

Results of the effect of the composition on insulin hormonal levels

| Group | Insulin (mU/L) |
|---|---|
| Group I | 0.27 ± 0.023 |
| Group II | 0.15 ± 0.008***[a] |
| Group III | 0.15 ± 0.005[ns b] |
| Group IV | 0.14 ± 0.005[ns b] |
| Group V | 0.22 ± 0.016*[b] |
| Group VI | 0.23 ± 0.021**[b] |

Data were analyzed by one way ANOVA followed by Dunnett's t test.
Number of animals in each group n = 6.
[a]Comparison made with control group.
[b]Comparison made with high fat diet group.
***$P < 0.001$
**$P < 0.01$
*$P < 0.05$
[ns]non significant.

Procedure:

Conclusion: The composition at 100 & 150 mg/kg b.w. showed significant increase (P<0.05, P<0.01 respectively) in insulin levels when compared to the high fat diet group (Group II).

Effect of the Composition on the Fecal Fatty Acid Estimation

TABLE 20

Effect of the composition on the fecal fatty acid estimation

| Group | Fecal fatty acid estimation |
|---|---|
| Group I | 1.0 ± 0.05 |
| Group II | 3.3 ± 0.13***[a] |
| Group III | 4.1 ± 0.26*[b] |
| Group IV | 2.3 ± 0.13**[b] |
| Group V | 2.4 ± 0.26**[b] |
| Group VI | 3.1 ± 0.26[ns b] |

Data were analyzed by one way ANOVA followed by Dunnett's t test.
Number of animals in each group n = 6.
[a]Comparison made with control group.
[b]Comparison made with high fat diet group.
***$P < 0.001$
**$P < 0.01$
*$P < 0.05$
[ns]non significant.

Conclusion: The composition at 50 & 100 mg/kg b.w. showed significant reduction (P<0.01) in fecal fatty acids when compared to the high fat diet group.

Overall, the in vivo anti-obesity studies of the composition revealed that it reduces body weight gain, reduces food intake, removes abdominal fat tissue, causes thermogenesis, improves the HDL levels, restores glucose levels, and has hepatoprotective effects.

EXAMPLE 6

Clinical Studies of Composition

A Prospective, Randomized, Double blind, Placebo controlled clinical trial to evaluate efficacy and safety of composition tablets in reducing the bodyweight in obese patients was carried out. A total 30 numbers of subjects were included in the study as per inclusion criteria. Subjects were randomized and equal no of subjects were assigned in composition treatment group A and placebo treatment group B. The clinical study conducted for 56 days at Sampoorna Healthcare and Amruth Poly clinic, Bangalore, India. The study was performed in fulfillment with Declaration of Helsinki, 2002. The protocol and patient informed consent form was reviewed and approved by appropriate independent ethics committees of Sampoorna Healthcare and Amruth Poly Clinic before the starting of the study. Subjects were on a treatment for 56 days and examined at weeks 0, 2, 4, 8 of the study. Volunteers followed up for the two weeks after treatment period that was $10^{th}$ week of the study. On $0^{th}$ week, subjects were examined for physical examination, anthropometric measurements, quality of life assessment and multiple laboratory tests which include biochemical parameters, HbA1c measurements and hematology parameters as baseline data. During $2^{nd}$ and $4^{th}$ visits anthropometric measurements, physical examination and any adverse events were reported. On $8^{th}$ week visit, physical examinations, anthropometric measurements, lipid profile, fasting blood glucose, HbA1c, quality of life assessment, adverse events, concomitant medications were recorded. All subjects were counseled for diet and exercise compliance at every visit. $10^{th}$ week visit was meant to examine vital signs, physical examination, recording of adverse effects or serious adverse events, concomitant medications, weight, BMI & waist circumference, Waist to hip ratio and waist to height ratio. The subjects were asked to take one tablet containing 500 mg of either composition or placebo three times a day for 08 weeks before breakfast and meals.

TABLE 21

Primary and secondary outcome of composition treated group

| No. | Parameters | Visit 1 | Visit 4 | Difference in % |
|---|---|---|---|---|
| 1 | Body weight(kg) | 82.5 ± 12.3 | 77.25 ± 12.9 | 6.36 |
| 2 | Body mass index (BMI kg/m$^2$) | 30.96 ± 1.76 | 28.92 ± 2.0 | 6.59 |
| 3 | Waist circumference (cm) | 101.25 ± 6.67 | 94.92 ± 5.9 | 6.25 |
| 4 | Hip circumference (cm) | 106.33 ± 2.05 | 101.91 ± 1.67 | 4.16 |
| 5 | Triglycerides (mg/dL) | 168.5 ± 73.56 | 143.83 ± 46.13 | 14.64 |
| 6 | Cholesterol (mg/dL) | 214.08 ± 33.2 | 187.91 ± 21.2 | 12.22 |
| 7 | LDL(mg/dL) | 138.27 ± 34.9 | 104.33 ± 25.73 | 24.55 |
| 8 | VLDL(mg/dL) | 33.7 ± 14.71 | 28.76 ± 9.22 | 14.66 |
| 9 | HDL | 42.1 ± 8.4 | 54.81 ± 5.2 | 30.19 |

TABLE 22

Primary and secondary outcome of Placebo treated group

| No. | Parameters | Visit 1 | Visit 4 | Difference in % |
|---|---|---|---|---|
| 1 | Body weight(kg) | 85.5 ± 10.9 | 84.95 ± 10.88 | 0.643 |
| 2 | Body mass index (BMI kg/m$^2$) | 32.33 ± 1.88 | 32.04 ± 1.81 | 0.90 |
| 3 | Waist circumference (cm) | 104.79 ± 5.36 | 104.42 ± 5.33 | 0.35 |
| 4 | Hip circumference (cm) | 108.83 ± 1.70 | 108.46 ± 1.73 | 0.34 |
| 5 | Triglycerides (mg/dL) | 188.5 ± 75.4 | 185.75 ± 74.68 | 1.46 |
| 6 | Cholesterol (mg/dL) | 204.91 ± 43.8 | 201.16 ± 43.2 | 1.83 |
| 7 | LDL (mg/dL) | 108.85 ± 59.7 | 107.75 ± 59.16 | 1.01 |
| 8 | VLDL (mg/dL) | 37.7 ± 15.08 | 37.15 ± 14.93 | 1.46 |
| 9 | HDL | 41.92 ± 4 | 41.93 ± 3.52 | 0.02 |

Clinical data suggest that composition is safe and has shown significant efficacy to reduce body weight and other obesity related complications.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

REFERENCES

1. OECD Guideline for the testing of chemicals-Repeated Dose 90-day Oral Toxicity Study in Rodents; TG 408, 21 Sept. 1998.
2. OECD Guideline No. 420, "Acute Oral Toxicity"—Fixed Dose Procedure 17 Dec. 2001.
3. Chougule A., Manjunath A. (2012), Anti-obesity drugs of Bhava prakasha nighantu: The literary survey. IJRAP, 3 (5), 650-654.
4. Juliana Aparecida Severi, Zeila Pinheiro Lima, Héllo Kushima, Alba Regina Monteiro Souza Brito, Lourdes Campaner dos Santos, Wagner Vilegas, Clélia Akiko HirumaLima (2009) Polyphenols with Antiulcerogenic Action from Aqueous Decoction of Mango Leaves (*Mangifera indica* L.). Molecules, 14, 1098-1110.
5. Ajila, C. M., Bhat, S. G., & Prasada Rao, U. J. S. (2007a). Valuable components of raw and ripe peels from two Indian mango varieties. Food Chemistry, 102, 1006-1011.
6. Aiyelaagbe O. O., Osamudiamen P. M. (2009) Phytochemical Screening for Active Compounds in *Mangifera indica* Leaves from Ibadan, Oyo State Plant Sciences Research, 2(1), 11-13.
7. Singh S. K., Sinha S. K., Prasad S. K., Kumar R., Bithu B. S., Kuma S. S., Singh P. (2011) Synthesis and evaluation of novel analogues of mangiferin as potent antipyretic. Asian Pacific Journal of Tropical Medicine, 866-869.
8. Gabino Garrido, Idania Rodeiro, Ivones Hernández, Gastón García, Gema Pérez, Nelson Merino, Alberto Núñez-Sellés, René Delgado (2009) In vivo acute toxicological studies of an antioxidant extract from *Mangifera indica* L. (Vimang), 32(1), 53-8.

What is claimed is:

1. A composition comprising:
    about 22% mangiferin,
    about 4% catechin,
    about 3% epicatechin
    about 0.4% quercetin dihydrate,
    4.5+/−0.42% gallic acid;
    0.93+/−0.23% 3,4 dihydroxy benzoic acid;
    1.2+/−0.34% methyl gallate;
    2.31+/−0.73% propyl gallate;
    0.48+/−0.08% pyrogallol;
    1.43+/−0.07% parahydroxy benzoic acid;
    0.33+/−0.06% vanillic acid;
    0.82+/−0.13% syringic acid;
    0.12+/−0.02% ferulic acid;
    0.76+/−0.14% ethyl gallate; and
    0.16+/−0.05% ellagic acid;
    wherein said composition has a total flavonoid content of about 29% and a total polyphenol content of about 19%, and
    wherein said composition is in an administration form selected from the group consisting of: a pill, tablet, capsule, lozenge, chewing gum, emulsion, topical patch, buccal patch, and gummy.

2. The composition of claim 1, wherein said composition further comprises an excipient.

3. The composition of claim 1, wherein said composition further comprises a sweetener, aromatic, flavoring, or combinations thereof.

4. The composition of claim 1, wherein said composition further comprises a mineral, protein, amino acid, carbohydrate, or combinations thereof.

5. The composition of claim 1, wherein said composition inhibits lipase activity by about 52% at a concentration of about 100 µg/ml in vitro.

\* \* \* \* \*